United States Patent [19]
Urmey

[11] Patent Number: 5,846,226
[45] Date of Patent: Dec. 8, 1998

[54] SPINAL-EPIDURAL ADMINISTRATION SYSTEM

[76] Inventor: William F. Urmey, One Flint Ave., Larchmont, N.Y. 10538

[21] Appl. No.: 854,558

[22] Filed: May 12, 1997

[51] Int. Cl.$^6$ .................................................. A61M 5/178
[52] U.S. Cl. .......................... 604/158; 604/161; 604/164; 604/165
[58] Field of Search ..................... 604/158, 161, 604/164, 165, 166, 272, 273, 274, 264

[56] References Cited

U.S. PATENT DOCUMENTS

| | | | |
|---|---|---|---|
| 4,233,974 | 11/1980 | Desecki et al. | 604/165 |
| 4,275,728 | 6/1981 | Merry | 604/165 |
| 4,609,370 | 9/1986 | Morrison | 604/165 |
| 4,973,312 | 11/1990 | Andrew | 604/158 |
| 4,973,313 | 11/1990 | Katsaros et al. | 604/165 |
| 5,160,323 | 11/1992 | Andrew | 604/158 |
| 5,255,691 | 10/1993 | Otten | 607/117 |
| 5,480,389 | 1/1996 | McWha et al. | 604/165 |

Primary Examiner—Wynn Wood Coggins
Assistant Examiner—Cris L. Rodriguez
Attorney, Agent, or Firm—Natter & Natter

[57] ABSTRACT

A spinal-epidural administration set includes a spinal needle having a hub and an increased diameter zone extending axially from the hub toward a distal tip. Equidistantly spaced teeth project radially from the zone. The spinal needle is inserted through a hub of an epidural needle whose distal end is positioned within an epidural space. The epidural needle hub includes a throat having a keyway formed of pair of opposed flanges spaced apart a distance sufficient to provide channels for the teeth to pass into a lumen of the epidural needle. When the tip of the spinal needle penetrates the dural membrane, the spinal needle is rotated to engage axially spaced adjacent teeth between the flanges, axially locking the spinal needle. A syringe may then be attached to the spinal needle hub. In order to provide additional extension of the spinal needle through the dural membrane without advancing the epidural needle in the epidural space, the epidural needle hub includes a removable barrel.

18 Claims, 5 Drawing Sheets

SPINAL-EPIDURAL ADMINISTRATION SYSTEM

BACKGROUND OF THE INVENTION

1. Field of the Invention

This invention relates generally to the administration of regional anesthesia and more particularly, to a system for facilitating the administration of transdural anesthesia within the subarachnoid space.

2. Antecedents of the Invention

The use of general anesthesia during surgical or other medical procedures has become less favored while there has been an increase in the use of regional anesthesia procedures. Among the contributing factors was that duration of recovery from the effects of general anesthesia was generally longer than recovery from the effects of regional anesthesia. This factor became significant in light of emphasis on reducing or eliminating post operative hospitalization, e.g. ambulatory surgery procedures. Managed health care providers have also placed emphasis upon minimizing hospitalization expenses. Other factors favoring regional anesthesia over general anesthesia included the increased risk factors associated with general anesthesia as opposed to regional anesthesia.

Regional anesthesia has been traditionally administered through either an epidural technique or a transdural technique. In the epidural technique, a sharp pointed hollow epidural needle was employed to pierce skin and spinal ligaments and extend into the epidural space. A catheter was then inserted through the lumen of the epidural needle, the needle was removed and a syringe containing anesthesia was coupled to the catheter for administration of anesthesia into the patient's epidural space to provide sustained or prolonged anesthesia during a surgical or other procedure.

Because the anesthesia was administered through a catheter which remained in the epidural space, anesthesia administration could continue, as needed, during a lengthy medical procedure and post operative administration was also available.

Among the disadvantages of the epidural technique was that since the anesthesia was administered into the epidural space, the reaction time was relatively slow and sufficient lead time prior to the surgical procedure was required to ensure that the patient was adequately anaesthetized.

An alternative regional anesthesia procedure, known as the transdural or subarachnoid technique, employed a relatively thin spinal needle which was extended through the epidural space through the dural membrane and into the subarachnoid space. A syringe containing anesthesia was then coupled to the hub of the spinal needle and administered into the subarachnoid space.

This procedure provided for rapid onset of an anesthetic block. Since only a single administration was provided, however, during prolonged medical procedures there was a need for the administration of additional anesthesia. A significant drawback was that punctures of the dural membrane resulted in leakage of cerebrospinal fluid which often led to severe postdural puncture headaches. To reduce cerebrospinal fluid leakage, spinal needles of thin gauge were employed and practitioners strived to avoid multiple punctures of the dural membrane.

Among the advances in regional anesthesia administration has been the combination of both transdural (spinal) and epidural techniques which provided the advantage of a rapid anesthetic block associated with the transdural technique as well as prolonged anesthesia associated with the epidural technique.

In the combined spinal-epidural technique, an epidural needle was first inserted into the epidural space, then a spinal needle having a length longer than that of the epidural needle was inserted through the lumen of the epidural needle and advanced to puncture the dural membrane. Spinal anesthetic was then administered by syringe through the spinal needle into the subarachnoid space, after which, the practitioner withdrew the spinal needle.

An epidural catheter was then inserted through the epidural needle and into the epidural space. The epidural needle was withdrawn, leaving the catheter in position for continued administration of anesthetic during and after the surgical procedure.

Among the problems associated with the combined spinal-epidural technique was that the spinal needle was free to move relative to the epidural needle whose position was relatively stable. This resulted in the danger of axially displacing the spinal needle, for example, withdrawing the needle from the subarachnoid space or advancing the needle too far within the subarachnoid space when the syringe was being attached to the spinal needle hub. The practitioner was required to steady the spinal needle against movement relative to the epidural needle with one hand and at the same time, attach the syringe to the hub of the spinal needle with the other hand.

Not only did axial movement constitute a vexing problem, including possible multiple punctures through the dural membrane, but, in addition, since the spinal needle was of a considerably thinner gage than the epidural needle and was required to be longer than the epidural needle, the portion of the spinal needle shaft which extended beyond the hub of the epidural needle was subject to bending with concomitant lumen constriction.

Additional problems encountered by practitioners when performing the spinal-epidural administration technique related to the fact that the anatomic dimensions of patients varied, particularly those dimensions defining the epidural space, the thickness of the dural membrane and the distance to the subarachnoid space.

Often, when the spinal needle was fully inserted into the epidural needle, due to the variations of anatomic dimensions, the spinal needle did not yet penetrate the dural membrane. The practitioner, having positioned the epidural needle in the epidural space, was reluctant to advance the epidural needle further into the epidural space to provide additional reach for the spinal needle because of the hazard of piercing the dural membrane with the large diameter epidural needle. In such instances, either a longer spinal needle was required or the epidural needle was required to be inserted further into the epidural space or the epidural needle was withdrawn and reinserted at a different location.

SUMMARY OF THE INVENTION

A system for spinal-epidural administration in accordance with the present invention includes a spinal needle having a thickened zone along its shaft, with the zone extending from a proximal hub toward the distal end of the needle. The zone includes equidistantly spaced radial teeth.

After the epidural needle is inserted into the patient such that its distal end is positioned within the epidural space, the spinal needle is then inserted through a hub of the epidural needle. A keyway is formed in a throat of the epidural needle hub. The keyway includes a pair of opposed arcuate flanges spaced apart by a pair of channels a distance sufficient to permit the teeth to pass.

The spinal needle shaft is extended into the epidural needle lumen until its tip reaches the patient's subarachnoid space. The spinal needle is then axially locked relative to the epidural needle by rotation of the spinal needle hub, such that the teeth are no longer registered with the channels.

With the spinal needle axially locked, the practitioner then attaches a syringe to the spinal needle hub. Since the portion spinal needle shaft which extends beyond the epidural needle hub comprises the reinforced zone of increased diameter as opposed to the diameter of the spinal needle shaft, the spinal needle will not readily bend.

In the event complete insertion of the spinal needle into the epidural needle lumen does not result in the tip of the spinal needle entering the subarachnoid space, the effective length of the spinal needle may be increased by removing a threaded barrel portion of the epidural needle hub.

From the foregoing compendium, it will be appreciated that it is an aspect of the present invention to provide a spinal-epidural administration system of the general character described which is not subject to the disadvantages of the antecedents of the invention aforementioned.

It is a feature of the present invention to provide a spinal-epidural administration system of the general character described with reduced likelihood of postdural puncture headaches.

A consideration of the present invention is to provide a spinal-epidural administration system of the general character described which simplifies the effective administration of regional anesthesia.

A further aspect of the present invention is to provide a spinal-epidural administration system of the general character described wherein a portion of the spinal needle shaft is reinforced to resist radial flexure and concomitant lumen obstruction.

An additional feature of the present invention is to provide a spinal-epidural administration system of the general character described which precludes axial movement of a spinal needle relative to an epidural needle.

Another consideration of the present invention is to provide a spinal-epidural administration system of the general character described wherein the position of a spinal needle within a patient's subarachnoid space may be axially fixed by rotation of the spinal needle.

Yet another aspect of the present invention is to provide a spinal-epidural administration system of the general character described which may be economically mass produced.

A further feature of the present invention is to provide a spinal epidural administration system of the general character described with relatively few components.

Yet another aspect of the present invention is to provide a spinal-epidural administration system of the general character described which is both reliable and simple to use.

An additional consideration of the present invention is to provide a spinal-epidural administration system of the general character described wherein the effective length of a spinal needle relative to an epidural needle may be increased.

A further feature of the present invention is to provide a spinal-epidural administration system of the general character described wherein an epidural needle hub includes a removable portion for selectively increasing the effective length of a spinal needle.

Other aspects, features and considerations of the present invention in part will be obvious and in part will be pointed out hereinafter.

With these ends in view, the invention finds embodiment in the various combinations of elements arrangements of parts and series of steps by which the aforesaid aspects, features and considerations are obtained, all as more fully described with reference to the accompanying drawings and the scope of which is more particularly pointed out and indicated in the appended claims.

BRIEF DESCRIPTION OF THE DRAWINGS

In the accompanying drawings in which is shown one of the various possible exemplary embodiments of the invention.

DESCRIPTION OF THE PREFERRED EMBODIMENT

Figure 1:
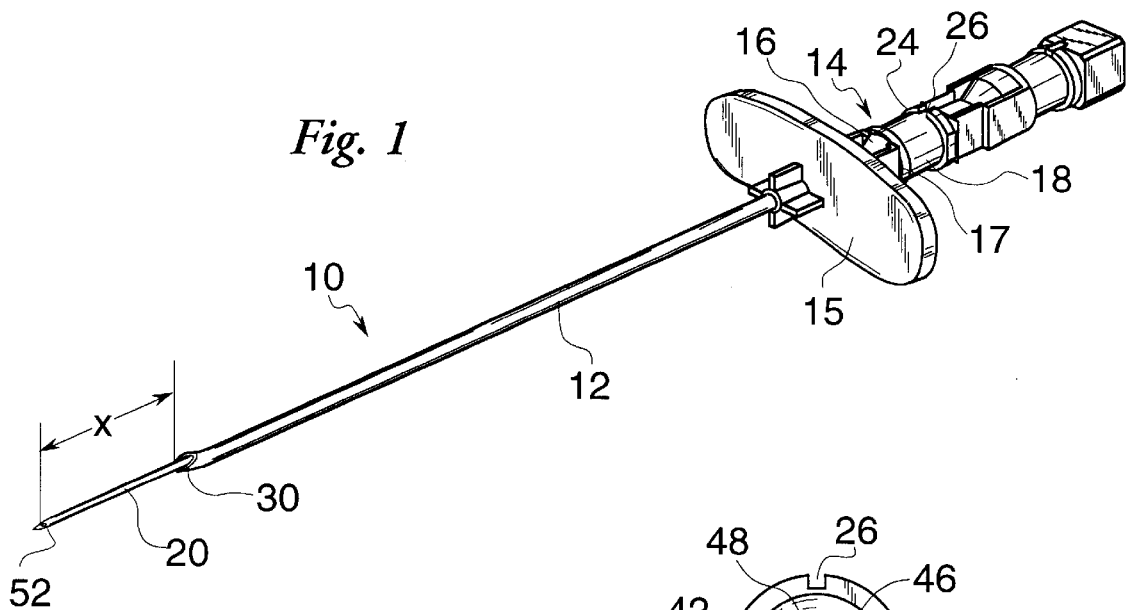
FIG. 1 is a perspective illustration of a spinal-epidural administration system constructed in accordance with and embodying the invention and illustrating a spinal needle seated within the lumen of an epidural needle and extended to its full length relative to the epidural needle.
Figure 3:
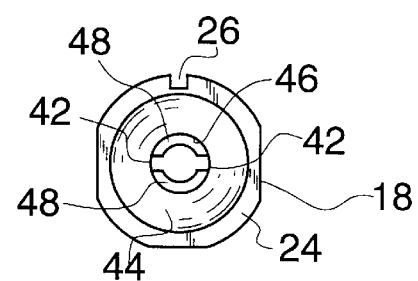
FIG. 3 is an auxiliary end view of a hub of the epidural needle, the same being taken substantially along the line 3—3 of FIG. 2 and illustrating a keyway formed in a throat of the hub.

Referring now in detail to the drawings, the reference numeral 10 denotes generally a spinal-epidural administration set constructed in accordance with and embodying the invention. The administration set 10 comprises an epidural needle shaft 12 having a hub assembly 14 which includes a transverse wing collar 15, enabling the practitioner to manipulate the needle. The hub assembly 14 includes a base 16 having a pair of panels 17 and a barrel 18. The barrel 18 of the hub assembly 14 includes a proximal end flange 24 having a Luer connector fitting 26.

A spinal needle having a shaft 20 and a hub assembly 22 is configured to be operatively positioned within a lumen 25 of the epidural needle shaft 12.

At the commencement of the spinal-epidural administration technique, the epidural needle carries a stylet having a hub which is fitted within the hub barrel 18. A sharp cutting tip 30 of the epidural needle is employed to penetrate the patient's dermal tissue adjacent the spine, with the stylet in place. Thereafter, the stylet is removed and a syringe is attached to the proximal end of the barrel 18 for applying fluid pressure through the epidural needle shaft while the epidural needle is advanced through the ligamentous tissue 32.

Figure 2:
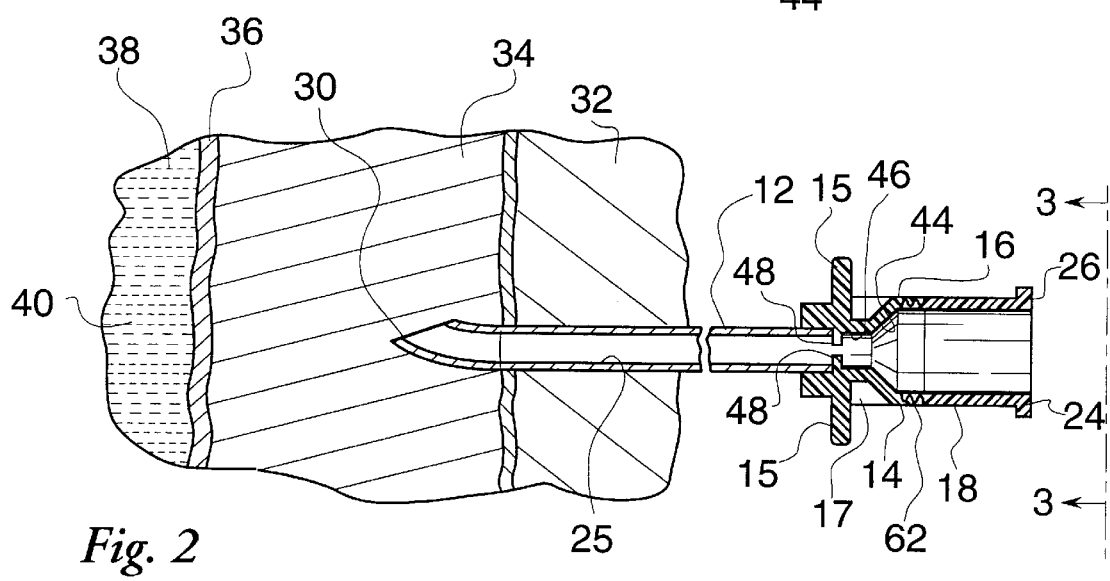
FIG. 2 is a fragmentary longitudinal sectional view of the epidural needle positioned within a patient's epidural space and illustrating surrounding anatomic structure.

Upon the tip 30 reaching the epidural space 34, the practitioner will sense a reduction in back pressure at the syringe. The syringe is then removed. It should be noted from an examination of FIG. 2 that axially positioned beyond the cutting tip 30 of the epidural needle is the patient's dural membrane 36 which defines the patient's subarachnoid space 38, carrying cerebrospinal fluid 40.

The epidural needle hub 14 includes a funnel surface 44 which leads to a constricted throat 46 at the entrance to the lumen 25. The throat 46 is constricted by a keyway formed of a pair of arcuate flanges 48 which are spaced apart by a pair of diagonally opposed channels 42.

Figure 4:
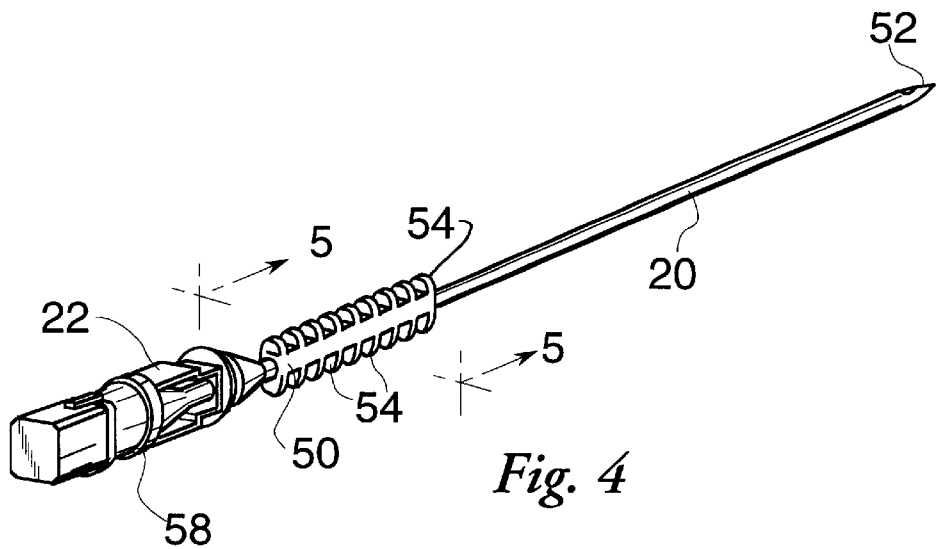
FIG.4 is a perspective view of the spinal needle illustrating a spinal needle hub and a reinforced increased diameter zone extending along the spinal needle shaft, with the zone including a plurality of radial teeth.
Figure 5:
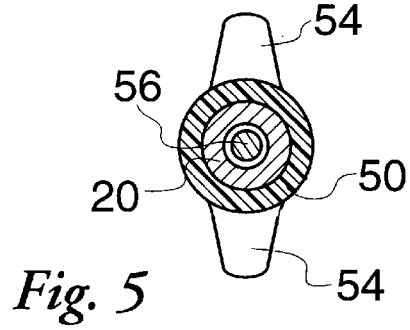
FIG. 5 is an enlarged scale sectional view through the increased diameter zone of the spinal needle, the same being taken substantially along the plane 5—5 of FIG. 4.

Turning now to FIGS. 4 and 5 wherein the spinal needle shaft 20 is illustrated, it will be seen that a stylet 56 is carried within the lumen of the spinal needle shaft, with the stylet having a hub 58. From the spinal needle hub assembly 22, a thickened zone 50 having a diameter greater than the diameter of the spinal needle shaft 20 and less than the diameter of the lumen 25, extends along the length of the spinal needle shaft toward a pencil point distal tip 52.

The thickened zone 50 includes diametrically opposed radially projecting teeth 54 which are axially equidistantly spaced from one another. The zone 50 may be integral with the hub 22 and need not overlie the spinal needle shaft along the entire length of the zone 50. For example, the proximal end of the spinal needle shaft may be anchored to only the distal end of the zone 50.

Figure 7:
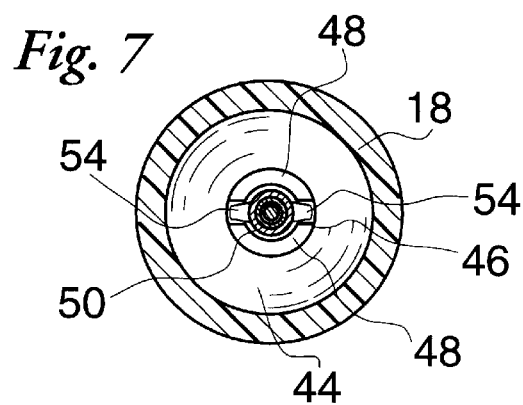
FIG. 7 is a greatly enlarged transverse sectional view through the epidural needle hub and the spinal needle, the same being taken substantially along the line 7—7 of FIG. 6 and more clearly showing the manner in which the teeth pass through the keyway.
Figure 6:
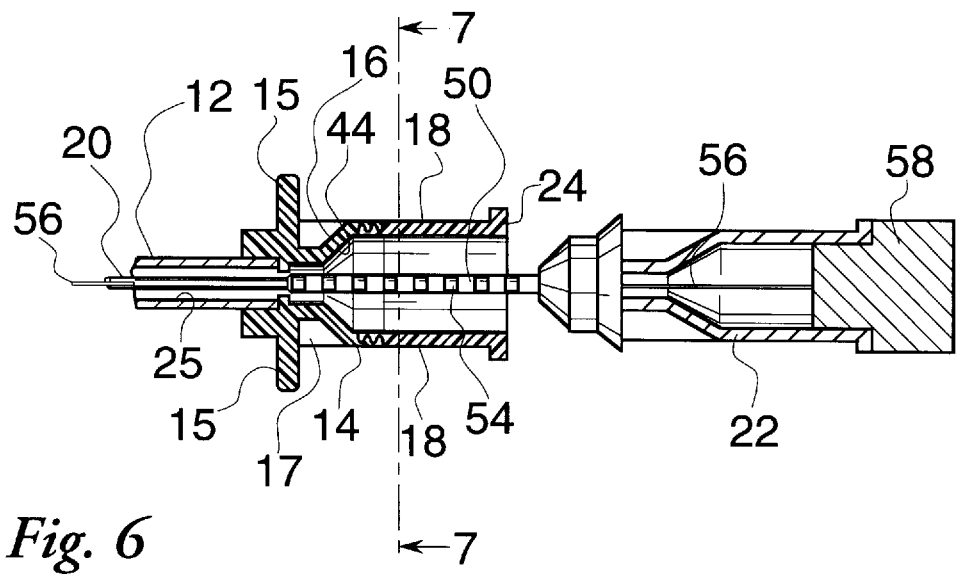
FIG. 6 is a fragmentary longitudinal sectional view through the epidural needle and illustrating the positioning of the spinal needle within the epidural needle.

Referring now to FIG. 6, it should be noted that the spinal needle shaft 20 is inserted through the epidural needle hub 14 and the throat 46 and into the lumen 25 of the epidural needle. The arcuate flanges 48 forming the keyway prevent entrance of the thickened zone 50 into the lumen except when the teeth 54 are registered with the channels 42. The orientation of the teeth 54 relative to the channels 42 for passage of the thickened zone 50 is illustrated in FIG. 6 and FIG. 7.

Figure 9:
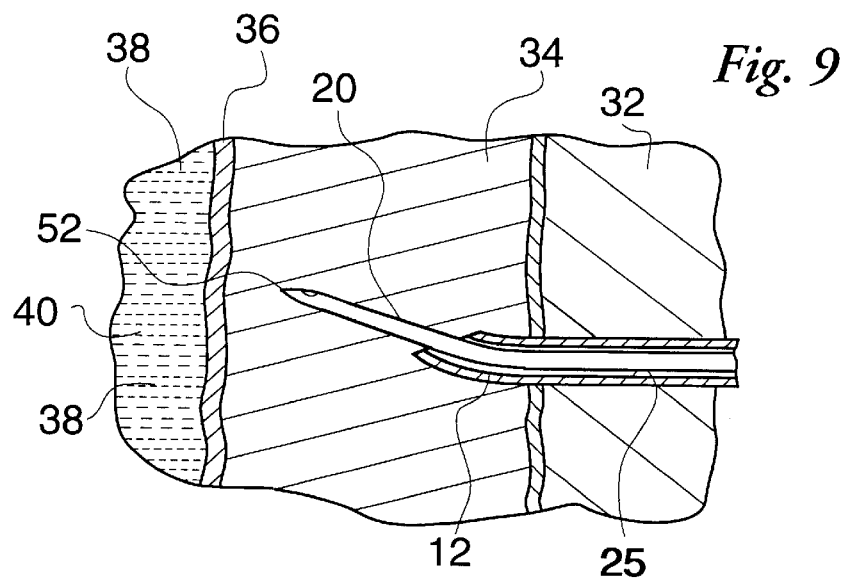
FIG. 9 is a fragmentary enlarged sectional view through the spinal needle similar to FIG. 2, however showing the extended portion of the spinal needle which projects beyond the tip of the epidural needle.

In FIG. 9 there is depicted the extension of the spinal needle from the tip of the epidural needle as the spinal needle is advancing into the epidural needle and prior to penetration of the dural membrane 36 by the tip 52.

Figure 8:
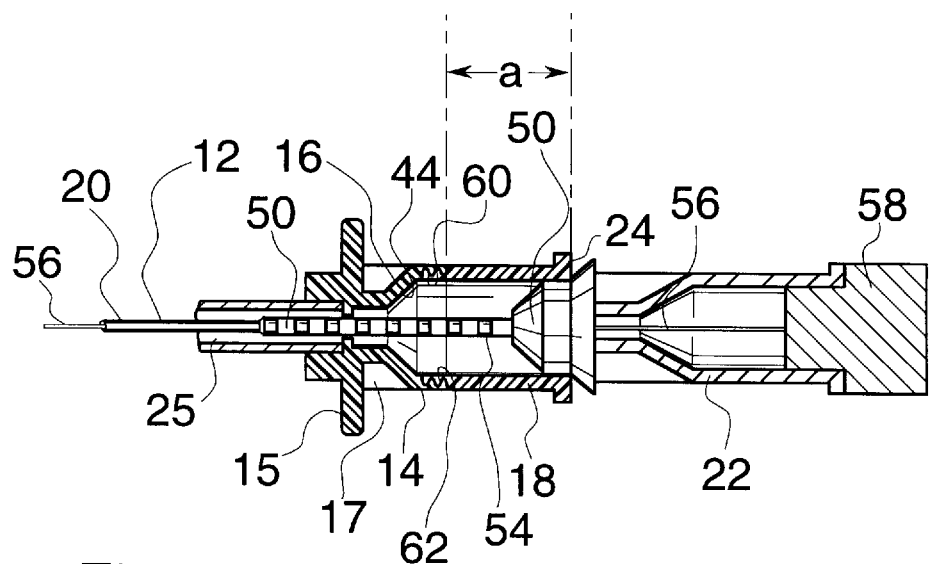
FIG. 8 is a longitudinal sectional view through the epidural needle and showing the spinal needle positioned for full extension from the tip of the epidural needle.

In some instances, depending upon the relative anatomic dimensions of the patient and the position of the tip 30 of the epidural needle, the spinal needle will reach maximum extension by engagement of the distal end of the spinal needle hub 22 against the barrel end flange 24, as illustrated in FIG. 8, prior to penetration of the dural membrane 36 by the tip 52.

Pursuant to the invention, in such instances, the spinal needle may be withdrawn and the barrel 18 removed. For such purpose, the hub assembly 14 includes internal threads 60 at the proximal end of the hub assembly base 16 which mate with external threads 62 formed on the distal end of the barrel 18.

After removal of the barrel 18 and reinsertion of the spinal needle, additional extension of the spinal needle will be permitted relative to the epidural needle. The effective length of the hub barrel is illustrated in FIG. 8 as being a dimension "a" while the maximum extension of the epidural needle with the barrel 18 in place, is indicated by the dimension "x" in FIG. 1.

Figure 10:
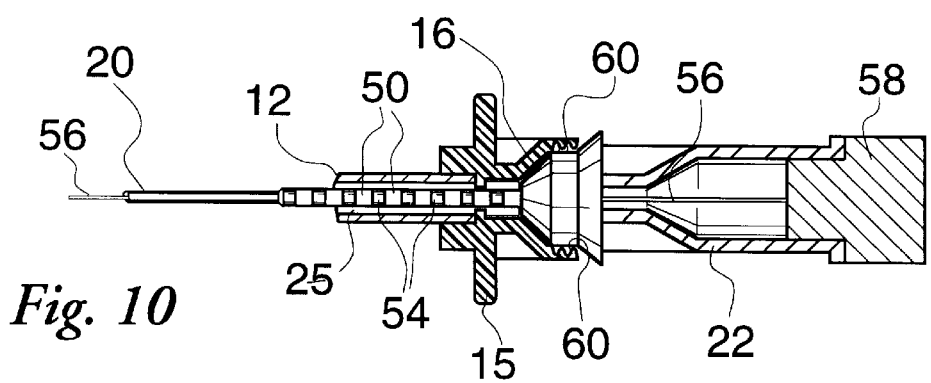
FIG. 10 is a longitudinal sectional view through the epidural needle and showing the position of the spinal needle hub relative to the epidural needle hub after a barrel of the epidural needle hub has been removed to provide further extension of the spinal needle.
Figure 11:
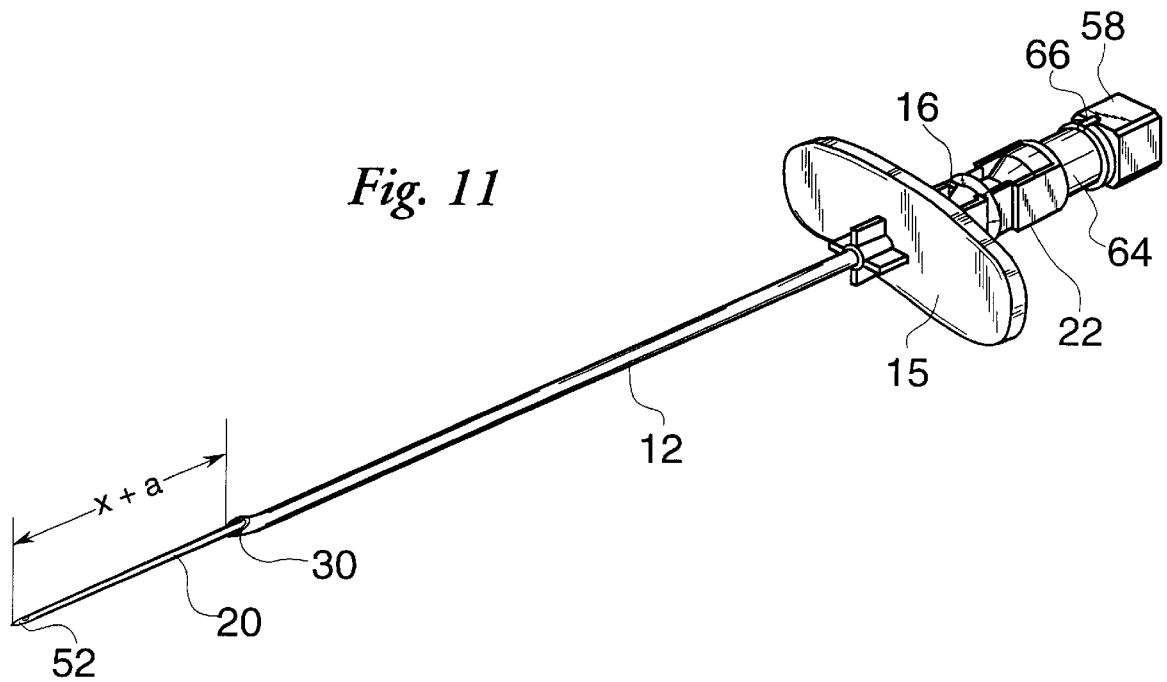
FIG. 11 is a perspective illustration of the spinal-epidural administration set as illustrated in FIG. 1 however, with the spinal needle extended an additional length after removal of the barrel.

The spinal needle may now be advanced to a maximum depth position wherein the spinal needle hub assembly 22 abuts against the base 16 of the hub assembly 14, as illustrated in FIG. 10. In such position, the maximum extension of the spinal needle comprises the original distance "x" plus the distance "a" as illustrated in FIG. 11.

Figure 12:
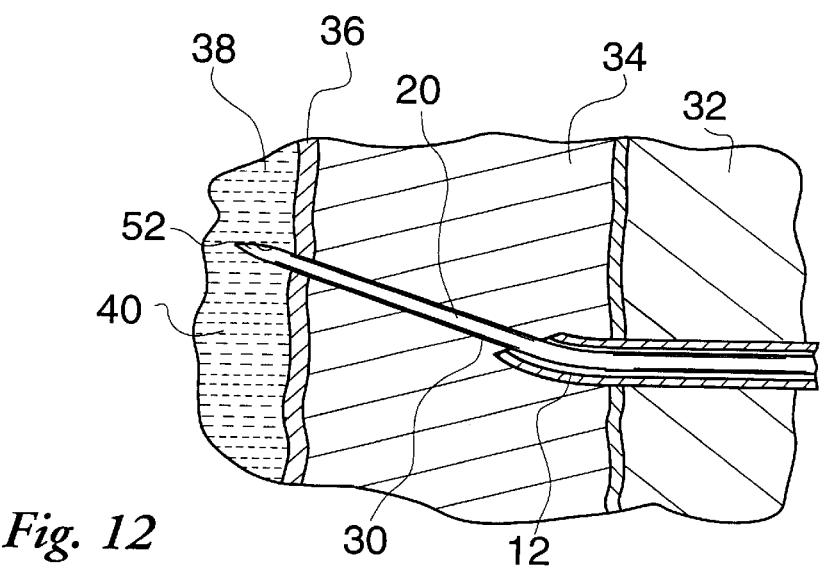
FIG. 12 is a fragmentary sectional view through the spinal needle and a portion of the patient's body and illustrating the position of the spinal needle within a subarachnoid space for administration of spinal anesthesia.

Depicted in FIG. 12 is the position of the tip 52 of the spinal needle 20 in the subarachnoid space 38 after having penetrated the dural membrane 36. The position of the tip 52 may be sensed by the practitioner not only as a result of feel, i.e. lack of resistance after penetrating the dural membrane 36 but, additionally, upon withdrawal of the stylet 56, cerebrospinal fluid 42 will appear.

Figure 13:
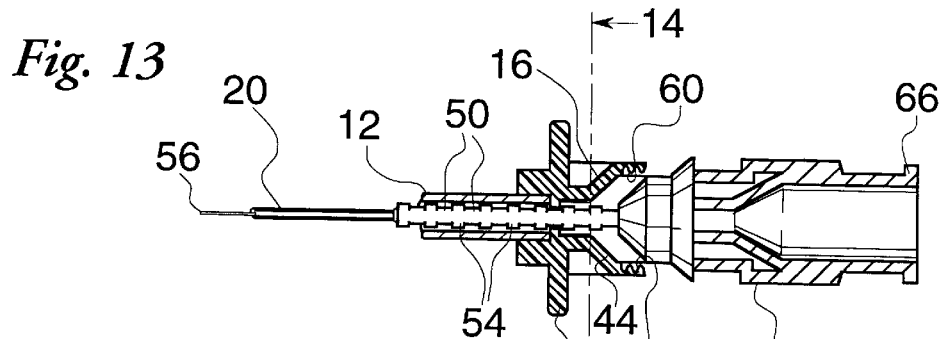
FIG. 13 is a longitudinal sectional view through the epidural needle and showing the spinal needle rotated to a position wherein it is locked against axial movement relative to the epidural needle.
Figure 14:
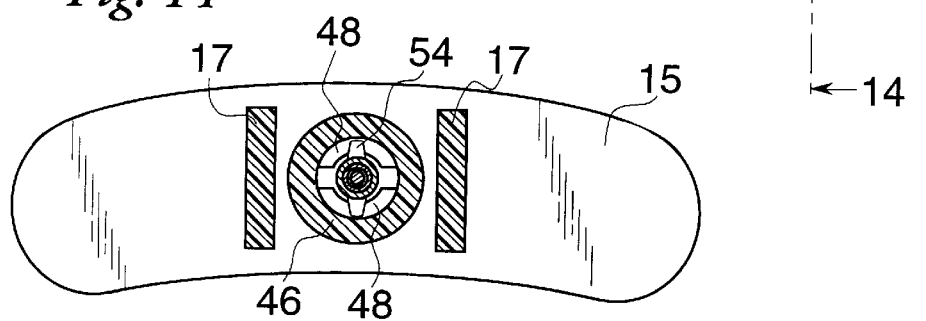
FIG. 14 is a sectional view through the spinal-epidural administration set, the same being taken substantially along the lines 14—14 of FIG. 13 and illustrating the position of the spinal needle teeth when the spinal needle is locked against axial movement.

FIG. 13 indicates the relative position of the spinal needle hub relative to the epidural needle hub when the spinal needle tip is in the subarachnoid space illustrated in FIG. 12. It should not be inferred, however, that removal of the barrel 18 will be required in all or most instances.

Once the spinal needle is within the subarachnoid space, the practitioner axially locks the spinal needle relative to the epidural needle by rotating the spinal needle hub 22 such that the teeth 54 are no longer registered with the channels 42. In the locked position, the arcuate flanges 48 will engage a pair of adjacent proximal teeth 54 to prevent further extension of the spinal needle into the epidural needle and will engage a pair of adjacent distal teeth 54 to prevent withdrawal of the spinal needle.

The practitioner may then attach a syringe to the spinal needle hub 22 at its syringe fitting and administer an appropriate dosage of spinal anesthesia. Thereafter, the spinal needle is rotated for registration of the teeth 54 with the channels 42 and then the spinal needle 20 is withdrawn from the epidural needle 12.

According to conventional procedure, if epidural administration is desired, a catheter is inserted through the lumen 25 of the epidural needle and into the epidural space 34, after which the epidural needle is withdrawn and conventional epidural anesthesia administered through the catheter.

It should be appreciated that the increased diameter thickened zone 50 not only carries the teeth 54 for axially locking the spinal needle but, in addition, serves to reinforce the proximal end of the spinal needle to reduce radially flexing or bending the spinal needle when a syringe is attached to the hub 22.

The needle shafts may be fabricated of conventional materials, e.g. stainless steel, while the respective hub assemblies are fabricated of plastic, for example. The increased diameter zone 50 of the spinal needle may be formed of plastic. Alternatively, the zone 50 may comprise a metal sleeve bonded around the spinal needle shaft or integral with the shaft with the teeth formed of metal or plastic.

Although the present invention has been described with reference to a combined spinal-epidural administration technique, it may be readily employed solely in conjunction with the transdural administration, in which case the epidural needle functions only as an introducer needle.

Thus it will be seen that there is provided a spinal-epidural administration system which achieves the various aspects, features and considerations of the present invention and which is well suited to meet the conditions of practical usage.

Since various possible embodiments might be made of the spinal epidural administration system of the present invention and since various changes might be made in the exemplary embodiment set forth herein without departing from the spirit of the invention, it is to be understood that all matter described herein is to be interpreted as illustrative and not in a limiting sense.

Having thus described the invention there is claimed as new and desired to be secured by Letters Patent:

1. A system for transdural administration of anesthesia, the system comprising: a first needle assembly, the first needle assembly including a needle shaft having an internal lumen, a hub fixed to one end of the shaft, the hub being in communication with the lumen, the lumen being open at the other end of the shaft, the shaft being of a length sufficient to enter into the epidural space of a patient, a second needle assembly, the second needle assembly comprising a second needle shaft, the second needle shaft being hollow, the second needle shaft having an outer diameter less than the diameter of the lumen, the second needle shaft being slidably receivable through the hub and into the lumen, and means for adjustably fixing a selected axial position of the second needle assembly relative to the first needle assembly upon rotation of one of the needle assemblies relative to the other needle assembly.

2. A system for transdural administration of anesthesia as constructed in accordance with claim 1 wherein the means for adjustably fixing the axial position comprises a keyway formed in one of the needle assemblies, the keyway having a channel, and means projecting radially from the other needle assembly, the other needle assembly being movable axially relative to the one needle assembly when the means projecting radially is registered with the channel and being locked against axial movement at the selected position when the means projecting radially is not registered with the channel.

3. A system for transdural administration of anesthesia as constructed in accordance with claim 2 wherein the means projecting radially is fixed to the other needle assembly, the means projecting radially comprising a first plurality of teeth.

4. A system for transdural administration of anesthesia as constructed in accordance with claim 3 including a second plurality of teeth, the second plurality of teeth projecting from surfaces of the other needle assembly at positions diametrically opposed to the first plurality of teeth, the keyway having a second channel.

5. A system for transdural administration of anesthesia as constructed in accordance with claim 3 wherein the first plurality of teeth are equidistantly axially spaced along a longitudinal axis of the other needle assembly.

6. A system for transdural administration of anesthesia as constructed in accordance with claim 2 wherein the hub includes a throat, the keyway being formed in the throat.

7. A system for transdural administration of anesthesia as constructed in accordance with claim 1, wherein the second needle assembly includes an axial zone having a length greater than the length of the hub, the axial zone having diameter greater than the diameter of the second needle shaft and less than the diameter of the lumen, whereby portions of the second needle assembly which may project beyond the hub are reinforced against radial flexure.

8. A system for transdural administration of anesthesia as constructed in accordance with claim 1 wherein the first needle assembly comprises an epidural needle and the second needle assembly comprises a spinal needle.

9. A system for transdural administration of anesthesia as constructed in accordance with claim 1 wherein the hub includes a base adjacent the first needle shaft and a barrel, a distal end of the barrel being connected to the bases, the barrel having a proximal end configured for engagement with a syringe, the second needle shaft being longer than the first needle shaft, the second needle shaft having a maximum extension from the other end of the first needle shaft when the second needle assembly is seated at the proximal end of the barrel, and means for removing the barrel from the base for increasing the maximum extension of the second needle shaft beyond the other end of the first needle shaft.

10. A system for transdural administration of anesthesia as constructed in accordance with claim 9 wherein the means for removing the barrel from the base comprises means forming a screw thread on the base and means forming a mating screw thread at the distal end of the barrel.

11. A spinal-epidural administration set comprising an epidural needle assembly, the epidural needle assembly including a needle shaft having an internal lumen, a hub fixed to one end of the shaft, the hub being in communication with the lumen, the lumen being open at the other end of the shaft, the shaft being of a length sufficient to enter the epidural space of a patient, a spinal needle assembly, the spinal needle assembly comprising a spinal needle shaft, the spinal needle shaft having an outer diameter less than the diameter of the lumen, the spinal needle shaft being slidably receivable through the hub and into the lumen, the hub including a base adjacent the epidural needle shaft and a barrel, one end of the barrel being connected to the base, the barrel having an other end configured for engagement with a syringe, the spinal needle shaft being longer than the epidural needle shaft, the spinal needle shaft having a maximum extension beyond the epidural needle shaft through the open end of the lumen when the spinal needle assembly is seated at the other end of the barrel, and means for disconnecting the barrel from the base for increasing the maximum extension of the spinal needle shaft from the open end of the lumen.

12. A spinal-epidural administration set as constructed in accordance with claim 11 wherein the means for disconnecting the barrel from the base of the hub comprises means forming a screw thread adjacent an end of the base and means forming a mating screw thread at the one end of the barrel.

13. A spinal-epidural administration set as constructed in accordance with claim 11 further including means for preventing axial movement of the spinal needle assembly relative to the epidural needle assembly upon rotation of one of the needle assemblies relative to the other needle assembly.

14. A spinal-epidural administration set as constructed in accordance with claim 13 wherein the means for preventing axial movement comprises a keyway formed in one of the needle assemblies, the keyway having a channel and means projecting radially from the other needle assembly, the spinal needle assembly being movable axially relative to the epidural needle assembly when the means projecting radially is registered with the channel and being locked against axial movement when the means projecting radially is not registered with the channel.

15. A system for transdural administration of anesthesia, the system comprising a first needle assembly, the first needle assembly including a needle shaft having an internal lumen, a hub fixed to one end of the shaft, the hub being in communication with the lumen, the lumen being open at the other end of the shaft, the shaft being of a length sufficient to enter the epidural space of a patient, a second needle assembly, the second needle assembly comprising a second needle shaft, the second needle shaft having a diameter less than the diameter of the lumen, the second needle shaft being slidably receivable through the hub and into the lumen, the second needle shaft being longer than the first needle shaft, the second needle shaft having a distal end and a proximal end, and means for reinforcing a portion of the second needle shaft which projects beyond the hub of the first needle shaft against radial flexure, the means for reinforcing comprising an increased diameter zone along the axis of the second needle shaft in the portion of the second needle shaft which projects beyond the hub, the increased diameter being greater than the diameter of the second needle shaft and less than the diameter of the lumen.

16. A system for transdural administration of anesthesia as constructed in accordance with claim 15 further including a second hub, the second hub being fixed relative to the proximal end of the second needle shaft, the zone being in communication with the second hub.

17. A system for transdural administration of anesthesia as constructed in accordance with claim 15 further including means for preventing axial movement of the second needle assembly relative to the first needle assembly upon rotation of one of the needle assemblies relative to the other needle assembly.

18. A spinal-epidural administration set comprising an epidural needle assembly, the epidural needle assembly including a needle shaft having an internal lumen, a hub fixed to one end of the shaft, the hub being in communication with the lumen, the lumen being open at the other end of the shaft, the shaft being of a length sufficient to enter the epidural space of a patient, a spinal needle assembly, the spinal needle assembly comprising a spinal needle shaft, the spinal needle shaft having an outer diameter less than the diameter of the lumen, the spinal needle shaft being slidably receivable through the hub and into the lumen, the hub including a base adjacent the epidural needle shaft and a barrel, one end of the barrel being connected to the base, the barrel having an other end configured for engagement with a syringe, the spinal needle shaft being longer than the epidural needle shaft, the spinal needle shaft having a maximum extension beyond the epidural needle shaft through the open end of the lumen when the spinal needle assembly is seated at the other end of the barrel, the barrel being separable from the base whereby the maximum extension of the spinal needle shaft from the open end of the lumen can be increased.

* * * * *